(12) United States Patent
Chen et al.

(10) Patent No.: US 12,186,727 B2
(45) Date of Patent: Jan. 7, 2025

(54) LED LIGHT SOURCE PHOTOCATALYTIC TUBULAR REACTOR AND APPLICATION THEREOF

(71) Applicants: Shanghai SynTheAll Pharmaceuticals Co., Ltd., Shanghai (CN); Shanghai STA Pharmaceutical R&D Co., Ltd., Shanghai (CN); Shanghai STA Pharmaceutical Product Co., Ltd., Shanghai (CN)

(72) Inventors: Like Chen, Shanghai (CN); Ruiheng Zhu, Shanghai (CN); Zhenbing Zhao, Shanghai (CN); Donglin Li, Shanghai (CN); Abdolsamad Tadayon, Shanghai (CN); Xiaoyong Fu, Shanghai (CN)

(73) Assignees: Shanghai SynTheAll Pharmaceuticals Co., Ltd., Shanghai (CN); Shanghai STA Pharmaceutical R&D Co., Ltd., Shanghai (CN); Shanghai STA Pharmaceutical Product Co., Ltd., Shanghai (CN)

( * ) Notice: Subject to any disclaimer, the term of this patent is extended or adjusted under 35 U.S.C. 154(b) by 300 days.

(21) Appl. No.: 17/200,184

(22) Filed: Mar. 12, 2021

(65) Prior Publication Data

US 2021/0283570 A1    Sep. 16, 2021

(30) Foreign Application Priority Data

Mar. 13, 2020    (CN) .......................... 202010177965.3

(51) Int. Cl.
  *B01J 19/12*    (2006.01)
  *B01J 19/00*    (2006.01)
  (Continued)

(52) U.S. Cl.
  CPC ......... *B01J 19/122* (2013.01); *B01J 19/0013* (2013.01); *B01J 19/02* (2013.01);
  (Continued)

(58) Field of Classification Search
  CPC .... B01J 19/122; B01J 19/124; B01J 123/125; B01J 19/126; B01J 19/129; B01J 19/14;
  (Continued)

(56) References Cited

U.S. PATENT DOCUMENTS

| | | | |
|---|---|---|---|
| 5,184,020 A * | 2/1993 | Hearst | B01J 19/123 422/186 |
| 8,673,157 B2 * | 3/2014 | Kolios | B01J 35/004 250/363.01 |

(Continued)

FOREIGN PATENT DOCUMENTS

| | | |
|---|---|---|
| CN | 102151534 A | 8/2011 |
| CN | 202683206 U | 1/2013 |

(Continued)

OTHER PUBLICATIONS

"Gas phase photocatalytic spiral reactor for fast and efficient pollutant degradation" Year: 2017 By Blommaerts et al (Year: 2017).*

(Continued)

*Primary Examiner* — Xiuyu Tai
(74) *Attorney, Agent, or Firm* — NIXON & VANDERHYE, PC

(57) ABSTRACT

Disclosed is an LED light source photocatalytic tubular reactor and application thereof. The LED light source photocatalytic tubular reactor comprises an LED light source, a temperature control chamber and a transparent reaction pipeline; the transparent reaction pipeline is located in the temperature control chamber; at least one side of the temperature control chamber is a light-transmitting plate; the LED light source provides a light source for the transparent (Continued)

reaction pipeline through the light-transmitting plate; and the transparent reaction pipeline has a diameter-to-length ratio of the inner diameter to the length of 0-0.1, but not 0. The LED light source continuous photocatalytic tubular reactor of the present disclosure can eliminate the scaling up effect, increase the yield and allow continuous production with an advantage of easy to use and low cost. The tubular reaction device of the present disclosure can also realize automatic control, which can effectively reduce personnel costs and improve production safety.

23 Claims, 1 Drawing Sheet

(51) Int. Cl.
  *B01J 19/02* (2006.01)
  *B01J 19/24* (2006.01)
  *C07C 17/06* (2006.01)
  *C07C 45/51* (2006.01)

(52) U.S. Cl.
  CPC ............ *B01J 19/243* (2013.01); *C07C 17/06* (2013.01); *C07C 45/513* (2013.01); *B01J 2219/00081* (2013.01); *B01J 2219/0295* (2013.01); *B01J 2219/0801* (2013.01); *B01J 2219/0871* (2013.01); *B01J 2219/1203* (2013.01)

(58) Field of Classification Search
  CPC . B01J 19/02; B01J 19/08; B01J 19/243; B01J 19/2435; B01J 19/244; B01J 9/2445; B01J 19/245; B01J 2219/00081; B01J 19/00083; B01J 19/00085; B01J 19/0013; B01J 2219/0295; B01J 2219/0801; B01J 2219/0871; B01J 2219/1203; B01J 19/128; B01J 19/123; B01J 19/127; B01J 19/2415; B01J 2219/00033; B01J 2219/00096; B01J 2219/192; B01J 2219/0877; B01J 2219/0875; B01J 2219/126; C07C 17/06; C07C 45/513; C02F 2201/3228; C02F 2201/3222; C02F 2201/3227; C02F 2201/003; C02F 2301/026; C02F 1/30; C02F 1/325; Y02W 10/37
  See application file for complete search history.

(56) References Cited

U.S. PATENT DOCUMENTS

| | | | |
|---|---|---|---|
| 9,938,165 B2* | 4/2018 | Taghipour | ............... C02F 1/325 |
| 2016/0346757 A1* | 12/2016 | Rubio Martinez | ....... C07F 5/06 |
| 2019/0062180 A1* | 2/2019 | Taghipour | .......... H05K 7/20272 |
| 2023/0107949 A1* | 4/2023 | Broersma | ................. C02F 1/30 |
| | | | 204/157.15 |

FOREIGN PATENT DOCUMENTS

| | | |
|---|---|---|
| CN | 106892800 A | 6/2017 |
| CN | 109621863 A | 4/2019 |
| CN | 112191203 A | 1/2021 |

OTHER PUBLICATIONS

"Photochemical Processes in Continuous-Flow Reactors—Chapter 1: Design Consideration of Continuous-Flow Photoreactors" Year: 2017 By Protti et al (Year: 2017).*

"Photocatalytic Membrane Reactors (PMRs) in Water Treatment: Configurations and Influencing Factors" Year: 2017 By Zheng et al (Year: 2017).*

"On the reliable measurement of specific absorption rates and intrinsic loss parameters in magnetic hyperthermia materials" Year: 2014 by Wildeboer et al (Year: 2014).*

Li et al. (Kangqiang Li et al., High-temperature dielectric properties and pyrolysis reduction characteristics of different biomass-pyrolusite mixtures in microwave field, Bioresource Technology 294 (2019) 122217) (Year: 2019).*

Chen et al. (Yuesu Chen et al., Continuous flow photochemical benzylic bromination of a key intermediate in the synthesis of a 2-oxazolidinone, Chem Photo Chem, 2 (2018) 906-912). (Year: 2018).*

Dallüge et al., "Comparison of direct and indirect contact heat exchange to improve recovery of bio-oil", Applied Energy 251 113346, 2019, 10 pages.

Buglioni et al., "Technological Innovations in Photochemistry for Organic Synthesis: Flow Chemistry, High-Throughput Experimentation, Scale-up, and Photoelectrochemistry", ACS Publications, Chemical Reviews, 2022, 155 pages.

Cantillo et al., "A Scalable Procedure for Light-induced Benzylic Brominations in Continuous Fiow", ACS Publications, JOC, Nov. 21, 2013, 7 pages.

Politano et al., "Light on the Horizon: Current Research and Future Perspectives in Flow Photochemistry", ACS Publications, OPR&D, Aug. 2, 2018, 18 pages.

* cited by examiner

LED LIGHT SOURCE PHOTOCATALYTIC TUBULAR REACTOR AND APPLICATION THEREOF

This application claims priority to Chinese Application No. 202010177965.3, filed Mar. 13, 2020, the entire contents of which is incorporated herein by reference.

TECHNICAL FIELD

The present disclosure relates to an LED light source photocatalytic tubular reactor and application thereof.

BACKGROUND

Photocatalytic preparation of trifluoromethyl compounds and brominated compounds is a chemical reaction frequently used in fine chemical production. The reaction formula is as follows:

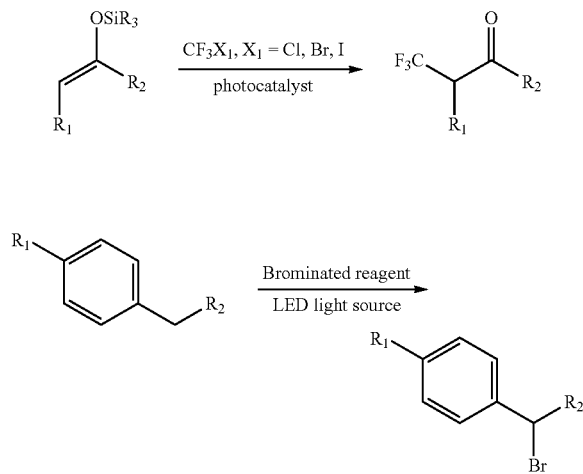

Under LED illumination conditions with specific wavelength, the reactant and the trifluoromethyl reagent or the brominated reagent are catalyzed by a catalyst to generate trifluoromethyl compounds or brominated compounds.

Batch reactors are conventionally used for the photocatalytic trifluoromethylation reaction. For example, patent CN202683206U discloses a photocatalytic reactor, which is only suitable for batch operation in laboratory, and it's difficult to scale up production. Patent application CN106892800A discloses a reaction in which a Schlenk tube is irradiated with a fluorescent lamp, and stirred for batch operation. When the reactor is enlarged, there are problems such as weakening of light absorption and slowing down of the reaction, which brings a great scaling-up effect. In addition, patent application CN102151534A discloses a photocatalytic reactor, whose light source placed outside the quartz reactor can be ultraviolet light, visible light or sunlight. The light passes through the quartz reactor to excite the photocatalyst and initiate the photocatalytic reaction, which can be operated intermittently or continuously, however, it does not solve the problem caused by scaling-up, i.e., the difficulty in customizing an explosion-proof LED light source with high-power and low-yield in the photocatalytic reaction. In another example, patent application CN109621863A discloses a photocatalytic reaction device, whose reactor comprises at least three layers of transparent plates and two layers of media, the light will be absorbed by the transparent plates and the media, and the light intensity irradiated on the reaction solution will be weakened, which affects the yield; meanwhile, the reactor is connected with more reaction units in series during the scaling-up process, so the flow rate increases, the flow rate of the interlayer medium will also increase, and the pressure inside the plates will inevitably increase. However, the transparent plates (mostly quartz or glass) are made of non-pressure resistant materials, which makes it difficult to seal and easy to leak; if the thickness of the transparent plates and the distance between the transparent plates are increased, the light intensity will be weakened with a great scaling-up effect; the material channels or temperature control channels will be etched on the surface of the transparent plates, which has the disadvantages of high cost and difficulty in replacement of reactor parts.

Therefore, there is a need for a photocatalytic reactor that can eliminate the scaling-up effect, increase the yield, and allow continuous production with convenient to use and low cost.

Content of the Present Invention

The technical problem to be solved in the present disclosure is that the photocatalytic reactor in the prior art can be only used for batch operation reaction, or has difficulty in to scaling up production and has the disadvantage of low yield, therefore, the present disclosure provides an LED light source photocatalytic tubular reactor and application thereof. The LED light source continuous photocatalytic tubular reactor of the present disclosure can eliminate the scaling-up effect, increase the yield and allow continuous production with an advantage of easy to use and low cost. The tubular reaction device of the present disclosure can also realize automatic control, which can effectively reduce personnel costs and improve production safety.

The present disclosure solves the above-mentioned technical problems by the following technical solutions:

The present disclosure provides an LED light source photocatalytic tubular reactor comprising an LED light source, a temperature control chamber and a transparent reaction pipeline;

the transparent reaction pipeline is located in the temperature control chamber;

at least one side of the temperature control chamber is a light-transmitting plate;

the LED light source provides a light source for the transparent reaction pipeline through the light-transmitting plate;

the transparent reaction pipeline has a diameter-to-length ratio of the inner diameter to the length of 0-0.1, but not 0.

In the present disclosure, the LED light source can be conventional in this field.

Preferably, the LED light source is an LED light source with variable power and wavelength, and the wavelength and power of the LED can be changed as required. For example, the LED light source can provide black light, blue light, green light, red light, white light, etc.

Preferably, the LED light source is a modular light source group. A plurality of the LED light sources can be integrated into a removable and detachable light source group that is controlled by software.

Wherein, the height and width of the LED modular light source group correspond to the area occupied by the transparent reaction pipeline which is coiled, thus providing a uniform light source for the transparent reaction pipeline.

Preferably, the LED light source is at a distance of 0-5 cm, more preferably 0-5 mm, and preferably the smaller the better, from the light-transmitting plate.

Preferably, the LED light source as a whole is designed as an explosion-proof LED light source device, which is suitable for scale-up production. Wherein, the explosion-proof LED light source device can prevent sparks, arcs or dangerous temperatures generated in use from being ignition sources of explosive mixtures at the installation site. The explosion-proof LED light source device is commercially available.

In the present disclosure, a temperature control medium can be circulated in the temperature control chamber so as to control temperature; or a temperature control pipeline can also be separately provided in the temperature control chamber to control temperature as well.

Further, the temperature control chamber can also be provided with an external flow temperature control system to precisely control the temperature of the system to eliminate the risks of thermal safety.

Preferably, a bracket is provided in the temperature control chamber for coiling the transparent reaction pipeline.

Wherein, preferably, the transparent reaction pipeline is coiled to form, but not limited to, a mosquito coil shape, an S shape or a snake shape.

Further, preferably, when a temperature control pipeline is separately provided in the temperature control chamber, the temperature control pipeline and the transparent reaction pipeline are spirally arranged and coiled.

Preferably, the temperature control chamber are equipped with pressure sensors at its inlet and outlet to monitor the pressure in real time.

The temperature control pipeline of the temperature control chamber has an inner diameter of preferably 1-50 mm, more preferably 2-20 mm.

When scaling up production, in order to reduce internal pressure and improve stability and safety, a method of split flow and pressure reduction can be adopted, in which a plurality of the temperature control chambers are connected in parallel with the external temperature control chambers.

In the present disclosure, preferably, the light-transmitting plate is a quartz plate or a glass plate.

The light-transmitting plate has a thickness of preferably 0-50 mm, more preferably 0-20 mm, for example 2-20 mm.

Preferably, the temperature control chamber is in the shape of a cube or a cylinder.

Wherein, preferably, both sides of the temperature control chamber are provided with light-transmitting plate; the LED light source is located on both sides of the outside of the temperature control chamber, and both sides are irradiated to increase the yield.

Preferably, except the part of the light-transmitting plate, the other parts of the temperature control chamber are made from stainless steel or polytetrafluoroethylene.

Preferably, the temperature control chamber has a temperature of −50° C.-100° C.

Preferably, the temperature control medium in the temperature control chamber is ethylene glycol and/or water.

In the present disclosure, the transparent reaction pipeline can be conventional in this field. The transparent reaction pipeline belongs to the type of tubular reactor, which is a tubular continuous operation reactor with a large length-to-diameter ratio.

Preferably, the transparent reaction pipeline has a circular shape, which is commercially available.

Preferably, the transparent reaction pipeline is made from tetrafluoroethylene-perfluoroalkoxy vinyl ether copolymer PFA or perfluoroethylene propylene copolymer FEP.

Preferably, the transparent reaction pipeline has a diameter-to-length ratio of the inner diameter to the length of 0-0.0005, but not 0.

Preferably, the transparent reaction pipeline has an inner diameter of 0-20 mm, but not 0; more preferably, 0-5 mm, but not 0.

Preferably, the transparent reaction pipeline is a plug flow tubular reactor.

When in use, preferably, the transparent reaction pipeline contains liquid, which has a linear velocity of no more than 3 m/s.

In order to scale up production, preferably, a combination of the LED light source photocatalytic tubular reactor in series or in parallel is obtained by connecting interfaces, which are made from tetrafluoroethylene-perfluoroalkoxy vinyl ether copolymer PFA, stainless steel or Hastelloy, to scale up production, wherein the flow rate can be increased to more than 10 times before series and/or parallel connection.

The present disclosure also provides a photocatalytic reaction device, which comprises the aforementioned LED light source photocatalytic tubular reactor.

Preferably, the photocatalytic reaction device further comprises a raw material tank, a feed pump, a back pressure valve and a product storage tank connected in sequence.

Wherein, preferably, the photocatalytic reaction device further comprises an integrated sealed box, which contains the temperature control chamber, the LED light source, and the transparent reaction pipeline.

Wherein, preferably, the photocatalytic reaction device further comprises a plurality of thermocouples, for example, three thermocouples.

Wherein, preferably, the thermocouples are located in a pipeline connecting the transparent reaction pipeline and the back pressure valve, and/or in an external flow temperature control system.

Wherein, preferably, the photocatalytic reaction device further comprises a plurality of pressure sensors.

Wherein, preferably, the pressure sensor is located in a pipeline connecting the feed pump and the transparent reaction pipeline, and/or in the external flow temperature control system.

The present disclosure also provides a method for preparing a trifluoromethyl compound or a brominated compound by using the aforementioned photocatalytic reaction device, which comprises the following steps:

S1. continuously supplying reaction raw materials to the transparent reaction pipeline in the aforementioned photocatalytic reaction device;

S2. carrying out photocatalysis to continuously prepare a trifluoromethyl compound or a brominated compound by controlling the reaction temperature using the temperature control chamber under the illumination of the LED light source.

In the present disclosure, the reaction raw materials refer to reaction substrates, trifluoromethylation reagents or brominated reagents, and catalysts; generally, the reaction raw materials are stored in the raw material tank and are pumped into the transparent reaction pipeline through the feed pump; after that, photocatalysis is performed to continuously prepare trifluoromethyl compounds or brominated compounds with the reaction temperature controlled by the temperature control chamber under the illumination of the LED light source. The obtained product flows into the product storage tank through the back pressure valve, thereby achieving a convenient continuous production.

In the present disclosure, the photocatalytic reaction device can also be used for photocatalytic reaction between liquid phases.

On the basis of common knowledge in the art, the various preferred conditions described above can be combined arbitrarily to obtain various preferred examples of the present disclosure.

The reagents and raw materials used in the present disclosure are commercially available.

The positive progress effects of present disclosure is as follows:

The LED light source continuous photocatalytic tubular reactor of the present disclosure can eliminate the scaling up effect, increase the yield, allowing a continuous production with easy to use and low in cost. The tubular reaction device of the present disclosure can also realize automatic control, which can effectively reduce personnel costs and improve production safety.

DESCRIPTION OF REFERENCE SIGNS

Figure 1:
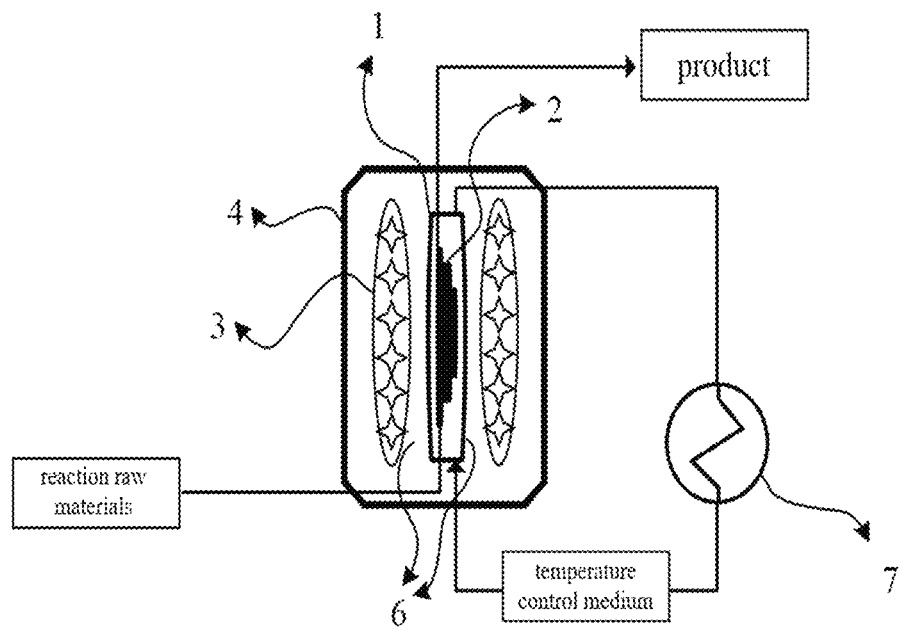
FIG. 1 shows a schematic diagram of the structure of the LED light source photocatalytic tubular reactor in Example 1.

Temperature control chamber 1
Transparent reaction pipeline 2
LED light source 3
Integrated sealed box 4
Thermocouple 5
Transparent quartz plate 6
External flow temperature control system 7
Raw material tank 8
Feed pump 9
LED light source photocatalytic tubular reactor 10
Back pressure valve 11
Product storage tank 12

DETAILED DESCRIPTION OF THE PREFERRED EMBODIMENT

The following examples further illustrate the present disclosure, but the present disclosure is not limited thereto. Unless specified otherwise, the experimental methods in the following examples are selected according to conventional methods and conditions, or according to the commodity specification.

Example 1

In Example 1, the LED light source photocatalytic tubular reactor 10 comprises an LED light source 3, a temperature control chamber 1 and a transparent reaction pipeline 2 (as shown in FIG. 1).

The temperature control chamber 1 has a cylindrical shape. Both sides of the temperature control chamber 1 are provided with transparent quartz plates 6. The transparent quartz plate 6 has a thickness of 10 mm Except the part of the transparent quartz plate 6, the other parts of the temperature control chamber 1 are made of stainless steel. The temperature control chamber 1 is provided with an external flow temperature control system 7. The temperature control pipeline of the temperature control chamber 1 has an inner diameter of 10 mm Both the inlet and the outlet of the temperature control chamber 1 are equipped with pressure sensors to monitor the pressure in real time. The temperature of the temperature control chamber 1 is −50° C.-100° C. The temperature control medium in the temperature control chamber 1 is ethylene glycol and water.

The LED light source 3 is an LED modular light source group with variable power and wavelength, which can change the wavelength and power of the LED by software controlling as required. The LED light source 3 as a whole is designed as an explosion-proof LED light source device, which is commercially available. The LED light source 3 is located on both sides of the outside of the temperature control chamber 1, and provides a light source for the transparent reaction pipeline 2 through the transparent quartz plate 6. The LED light source 3 and the light-transmitting plate has a distance of 1 mm.

The transparent reaction pipeline 2 is a plug flow tubular reactor. The transparent reaction pipeline 2 has a circular shape, which is commercially available. The transparent reaction pipeline 2 is made from tetrafluoroethylene-per-fluoroalkoxy vinyl ether copolymer PFA. When in use, the liquid in the transparent reaction pipeline 2 has a linear velocity of no more than 3 m/s.

The transparent reaction pipeline 2 is located in the temperature control chamber 1. A bracket is provided in the temperature control chamber 1 for coiling the transparent reaction pipeline 2. The transparent reaction pipeline 2 is coiled to form a shape of mosquito coil.

The inner diameter to the length of the transparent reaction pipeline 2 has a diameter-to-length ratio of the inner diameter to the length of 0.0005. The transparent reaction pipeline 2 has an inner diameter of 5 mm. The height and width of the LED modular light source group correspond to the area occupied by the transparent reaction pipeline 2 which is coiled, thereby providing a uniform light source for the transparent reaction pipeline 2.

Figure 2:
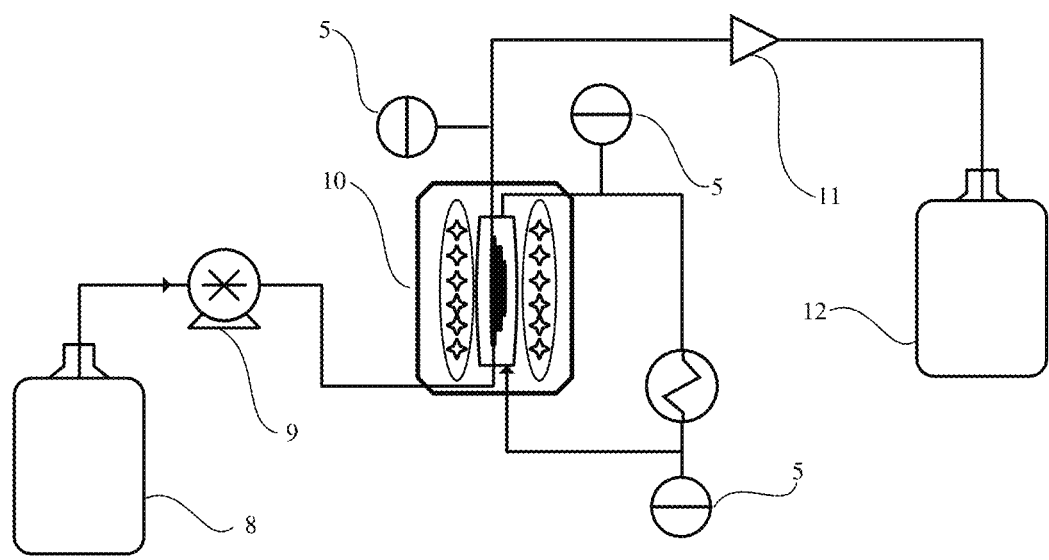
FIG. 2 shows an exemplary flow chart of the photocatalytic reaction device in Example 1.

The photocatalytic reaction device in Example 1 comprises the aforementioned LED light source photocatalytic tubular reactor 10 (as shown in FIG. 2).

The photocatalytic reaction device also includes a raw material tank 8, a feed pump 9, a back pressure valve 11 and a product storage tank 12, which are connected in sequence.

The photocatalytic reaction device also comprises an integrated sealed box 4, which contains a temperature control chamber 1, an LED light source 3, and a transparent reaction pipeline 2.

The photocatalytic reaction device further comprises three thermocouples 5, which are located in the pipeline connecting the transparent reaction pipeline 2 and the back pressure valve 11, and in the external flow temperature control system 7.

The photocatalytic reaction device further comprises a plurality of pressure sensors, which are not only located at the inlet and outlet of the temperature control chamber 1, but also located in the pipeline connecting the feed pump 9 and the transparent reaction pipeline 2.

In Example 1, when using the aforementioned photocatalytic reaction device to prepare a trifluoromethyl compound or a brominated compound, it comprises the following steps:

S1. continuously supplying the reaction raw materials to the transparent reaction pipeline 2 in the aforementioned LED light source photocatalytic tubular reactor 10;

S2. carrying out photocatalysis to continuously prepare a trifluoromethyl compound or a brominated compound by controlling the reaction temperature using the temperature control chamber 1 under the illumination of the LED light source 3.

The reaction raw materials are the reaction substrate, trifluoromethylation reagent and catalyst; the reaction raw materials were all stored in the raw material tank 8, and the reaction raw materials were pumped into the transparent reaction pipeline 2 through the feed pump 9; after that, under the illumination of the LED light source 3, with the reaction temperature controlled by the temperature control chamber 1, the corresponding trifluoromethyl compounds were continuously prepared by photocatalysis, and the obtained product flowed into the product storage tank 12 through the back pressure valve 11, thereby achieving a convenient continuous production.

EXAMPLE OF EFFECTS

The scaling up effect can be successfully eliminated by the device of Example 1 and the trifluoromethylation was fed at a flow rate of 200 L/h, and the reaction is complete.

If the reaction scale is enlarged by a factor of 2, it is only necessary to increase the flow rate by 2 times, and connect the LED light source photocatalytic tubular reactor 10 as described in Example 1 in series or in parallel (connected via the interface made from tetrafluoroethylene-perfluoroalkoxy vinyl ether copolymer PFA), with a conversion rate of 100%, and a yield of over 80%; currently, the bromination is realized with 5000 L feed per day, and the yield is over 90%.

What is claimed is:

1. An LED light source photocatalytic tubular reactor, comprising an LED light source, a temperature control chamber and a transparent reaction pipeline;
   wherein the transparent reaction pipeline is coiled and located in the temperature control chamber, wherein a temperature control medium is circulated in the temperature control chamber when in use, or a temperature control pipeline is separately provided in the temperature control chamber;
   wherein the temperature control chamber has two sides, and each side of the temperature control chamber is a light-transmitting plate;
   the LED light source is a modular LED light source group, which includes two modular light sources each located on one of the two sides outside of the temperature control chamber, and provides a light source for the transparent reaction pipeline through the light-transmitting plate on each of the two sides;
   the transparent reaction pipeline has a diameter-to-length ratio of the inner diameter to the length of 0-0.1, but not 0; and
   wherein the transparent reaction pipeline is a plug flow reactor.

2. The LED light source photocatalytic tubular reactor according to claim 1, wherein
   each of the two modular LED light sources is located at a distance of 0-5 cm from the light-transmitting plate on one of the two sides outside of the temperature control chamber.

3. The LED light source photocatalytic tubular reactor according to claim 1, wherein the temperature control medium in the temperature control chamber is ethylene glycol or water.

4. The LED light source photocatalytic tubular reactor according to claim 1, further comprising an external flow temperature control system.

5. The LED light source photocatalytic tubular reactor according to claim 1, wherein the transparent reaction pipeline is coiled to form a mosquito coil shape or an S shape:
   wherein the temperature control pipeline is separately provided in the temperature control chamber, and the temperature control pipeline and the transparent reaction pipeline are spirally arranged and coiled.

6. The LED light source photocatalytic tubular reactor according to claim 1, wherein the transparent reaction pipeline is circular pipeline:
   or, the transparent reaction pipeline has a diameter-to-length ratio of the inner diameter to the length of 0-0.0005, but not 0;
   or, the transparent reaction pipeline has an inner diameter of 0-20 mm, but not 0;
   or, when in use, the transparent reaction pipeline contains liquid, which has a linear velocity of no more than 3 m/s.

7. A photocatalytic reaction device, wherein the photocatalytic reaction device comprises (1) the LED light source photocatalytic tubular reactor according to claim 1; and (2) a raw material tank, a feed pump, a back pressure valve and a product storage tank connected in sequence.

8. The photocatalytic reaction device according to claim 7, wherein the photocatalytic reaction device further comprises a plurality of thermocouples.

9. A method for preparing a trifluoromethyl compound or a brominated compound by using the photocatalytic reaction device according to claim 7, wherein, the method comprises the following steps:
   S1. continuously supplying reaction raw materials to the transparent reaction pipeline in the photocatalytic reaction device according to claim 7;
   S2. carrying out photocatalysis to continuously prepare the trifluoromethyl compound or the brominated compound by controlling the reaction temperature using the temperature control chamber under the illumination of the LED light source.

10. A method for preparing a trifluoromethyl compound or a brominated compound by using the photocatalytic reaction device according to claim 8, wherein, the method comprises the following steps:
    S1. continuously supplying reaction raw materials to the transparent reaction pipeline in the photocatalytic reaction device according to claim 8;
    S2. carrying out photocatalysis to continuously prepare the trifluoromethyl compound or the brominated compound by controlling the reaction temperature using the temperature control chamber under the illumination of the LED light source.

11. The LED light source photocatalytic tubular reactor according to claim 2, wherein the LED light source is at a distance of 0-5 mm from the light-transmitting plate.

12. The LED light source photocatalytic tubular reactor according to claim 5, wherein the light-transmitting plate has a thickness of 0-20 mm:
    and the temperature control pipeline of the temperature control chamber has an inner diameter of 2-20 mm.

13. The LED light source photocatalytic tubular reactor according to claim 12, wherein the light-transmitting plate has a thickness of 2-20 mm.

14. The LED light source photocatalytic tubular reactor according to claim 1, wherein the transparent reaction pipeline has an inner diameter of 0-5 mm, but not 0.

15. The photocatalytic reaction device according to claim 8, wherein the plurality of thermocouples are located in a pipeline connecting the transparent reaction pipeline and the back pressure valve, or, in an external flow temperature control system; and
- a pressure sensor is located in a pipeline connecting the feed pump and the transparent reaction pipeline, or in the external flow temperature control system.

16. The photocatalytic reaction device according to claim 8, wherein the photocatalytic reaction device comprises three thermocouples.

17. A method for preparing a trifluoromethyl compound or a brominated compound by using the photocatalytic reaction device according to claim 16, wherein, the method comprises the following steps:
- S1. continuously supplying reaction raw materials to the transparent reaction pipeline in the photocatalytic reaction device according to claim 16;
- S2. carrying out photocatalysis to continuously prepare the trifluoromethyl compound or the brominated compound by controlling the reaction temperature using the temperature control chamber under the illumination of the LED light source.

18. The LED light source photocatalytic tubular reactor according to claim 1, wherein each of the two modular LED light sources is located at a distance of 0-5 mm from the light-transmitting plate on one of the two sides outside of the temperature control chamber.

19. The LED light source photocatalytic tubular reactor according to claim 1, wherein the height and width of the modular LED light source group correspond to the area occupied by the transparent reaction pipeline, thereby providing a uniform light source for the transparent reaction pipeline.

20. The LED light source photocatalytic tubular reactor according to claim 1, wherein the temperature control medium is circulated in the temperature control chamber when in use.

21. The LED light source photocatalytic tubular reactor according to claim 1, wherein the temperature control pipeline is separately provided in the temperature control chamber.

22. An LED light source photocatalytic tubular reactor, comprising an LED light source, a temperature control chamber and a transparent reaction pipeline: wherein:
- the transparent reaction pipeline is a plug flow reactor, which is coiled and located in the temperature control chamber;
- the temperature control chamber has a cylindrical shape having two sides, wherein each of the two sides of the cylinder is a light-transmitting plate;
- the LED light source is a modular LED light source group, which includes two modular LED light sources, wherein each of the two modular LED light sources is located at a distance of 0-5 mm from the light-transmitting plate on one of the two sides outside of the temperature control chamber, and provides a light source for the transparent reaction pipeline through the light-transmitting plate on each of the two sides; wherein the height and width of the modular LED light source group correspond to the area occupied by the coiled transparent reaction pipeline, thereby providing a uniform light source for the transparent reaction pipeline;
- the transparent reaction pipeline has a diameter-to-length ratio of the inner diameter to the length of 0-0.1, but not 0; and
- wherein a temperature control medium is circulated in the temperature control chamber when in use.

23. An LED light source photocatalytic tubular reactor, comprising: an LED light source, a temperature control chamber and a transparent reaction pipeline: wherein:
- the transparent reaction pipeline is a plug flow reactor, which is coiled and located in the temperature control chamber;
- the temperature control chamber has a cylindrical shape having two sides, wherein each of the two sides of the cylinder is a light-transmitting plate;
- the LED light source is a modular LED light source group, which includes two modular LED light sources, wherein each of the two modular LED light sources is located at a distance of 0-5 mm from the light-transmitting plate on one of the two sides outside of the temperature control chamber, and provides a light source for the transparent reaction pipeline through the light-transmitting plate on each of the two sides; wherein the height and width of the modular LED light source group correspond to the area occupied by the coiled transparent reaction pipeline, thereby providing a uniform light source for the transparent reaction pipeline;
- the transparent reaction pipeline has a diameter-to-length ratio of the inner diameter to the length of 0-0.1, but not 0; and
- wherein a temperature control pipeline is separately provided in the temperature control chamber, and the temperature control pipeline and the transparent reaction pipeline are spirally arranged and coiled.

\* \* \* \* \*